United States Patent [19]

Kabbe et al.

[11] 4,237,162

[45] Dec. 2, 1980

[54] COMBATING ARTHROPODS WITH 2-AND 4-SUBSTITUTED-CHROMANES

[75] Inventors: Hans-Joachim Kabbe, Leverkusen; Arno Widdig, Odenthal; Wilhelm Stendel, Wuppertal; Peter Roessler, Berg.Gladbach, all of Fed. Rep. of Germany

[73] Assignee: Bayer Aktiengesellschaft, Leverkusen, Fed. Rep. of Germany

[21] Appl. No.: 947,286

[22] Filed: Sep. 29, 1978

[30] Foreign Application Priority Data

Oct. 7, 1977 [DE] Fed. Rep. of Germany ....... 2745305

[51] Int. Cl.³ .................. C07D 311/38; A61K 31/35
[52] U.S. Cl. .................. 424/283; 260/345.2; 260/345.5; 260/326.8; 542/400; 546/196; 546/269
[58] Field of Search .................. 260/345.2, 345.5; 424/283; 542/400

[56] References Cited

U.S. PATENT DOCUMENTS

| | | | |
|---|---|---|---|
| 3,704,323 | 11/1972 | Krapcho | 260/345.2 |
| 3,753,985 | 8/1973 | Gavin et al. | 260/345.2 |
| 3,755,372 | 8/1973 | Irmscher et al. | 260/345.2 |

FOREIGN PATENT DOCUMENTS 2639671 4/1977 Fed. Rep. of Germany ........ 260/345.2

*Primary Examiner*—Nicky Chan
*Attorney, Agent, or Firm*—Sprung, Felfe, Horn, Lynch & Kramer

[57] ABSTRACT

Chromane derivatives of the formula

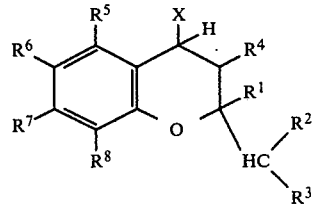

in which
R¹ to R⁴, which need not be identical, each represents hydrogen, an optionally substituted alkyl, alkenyl, cycloalkyl, aryl, aralkyl or alkoxycarbonyl radical, carboxyl or aminoalkyl,
R² can alternatively represent amino or optionally substituted dialkylamino, or R¹ and R² conjointly with the adjoining carbon atoms can form an optionally substituted carbocyclic or heterocyclic ring,
R⁵ to R⁸, which need not be identical, each represents hydrogen, halogen, hydroxyl, nitro, cyano, carboxyl, an optionally substituted alkyl, alkenyl, cycloalkyl, aryl, aralkyl, alkoxy, aralkoxy, aryloxy, alkoxycarbonyl, alkylamino or dialkylamino radical, amino or acylamino, and two of the radicals, which are in the o-position to one another, can represent tetramethylene or the radical —CH=CH—CH=CH—, and
X represents OH or the —NR⁹R¹⁰ radical, wherein
R⁹ and R¹⁰, which may be identical or different, each represents hydrogen or optionally substituted alkyl, alkenyl, cycloalkyl, aryl or aralkyl, or R⁹ and R¹⁰ conjointly with the adjoining nitrogen atom form a ring which optionally contains one or more further hetero-atoms,
or optionally, when X is —NR⁹R¹⁰, a salt thereof, in which
X is a hydroxy or amino radical, and
R¹ to R⁸ can be hydrogen or various organic radicals, or salts thereof possess arthropodicidal properties. Those compounds wherein R¹ and R² conjointly with the adjoining carbon atoms forms a carbocyclic or heterocyclic ring are new.

6 Claims, No Drawings

COMBATING ARTHROPODS WITH 2-AND 4-SUBSTITUTED-CHROMANES

The present invention relates to and has for its objects the provision of particular new arthropodicidal compositions containing 2- and 4-substituted chromanes, and methods for producing such compounds and for using such compounds in a new way especially for combating pests, e.g. insects, with other and further objects becoming apparent from a study of the within specification and accompanying examples.

The present invention relates to the use as arthropodicides, especially as insecticides and acaricides, of certain chromane derivatives, some of which are known.

It is known that some naturally occurring chromenes, for example Precocene I and Precocene II, exhibit a development-inhibiting action in insects and can therefore act as insecticides (see Chem. Eng. News 1976, No. 16, page 19). However, their action is not always satisfactory, above all if low concentrations are used.

It has now been found that the chromane derivatives of the general formula

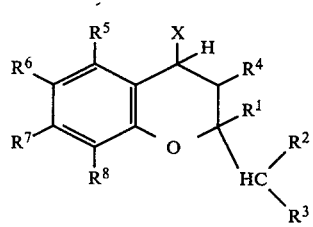

(I)

in which

R¹ to R⁴, which need not be identical, each represents hydrogen, an optionally substituted alkyl, alkenyl, cycloalkyl, aryl, aralkyl or alkoxycarbonyl radical, carboxyl or aminoalkyl, R² can alternatively represent amino or optionally substituted dialkylamino, or R¹ and R² conjointly with the adjoining carbon atoms can form an optionally substituted carbocyclic or heterocyclic ring, R⁵ to R⁸, which need not be identical, each represents hydrogen, halogen, hydroxyl, nitro, cyano, carboxyl an optionally substituted alkyl, alkenyl, cycloalkyl, aryl, aralkyl, alkoxy, aralkoxy, aryloxy, alkoxycarbonyl, alkylamino or dialkylamino radical, amino or acylamino, and two of the radicals, which are in the o-position to one another, can represent tetramethylene or the radical —CH=CH—CH=CH—, and X represents OH or the —NR⁹R¹⁰ radical, wherein R⁹ and R¹⁰, which may be identical or different, each represents hydrogen or optionally substituted alkyl, alkenyl, cycloalkyl, aryl or aralkyl, or R⁹ and R¹⁰, conjointly with the adjoining nitrogen atom, form a ring which optionally contains one or more further heteroatoms, as well as the salts of the compounds in which X represents the NR⁹R¹⁰ radial, exhibit powerful development-inhibiting properties in arthropods, in particular insects and arachnids.

Accordingly, the present invention provides an arthropodical composition containing as active ingredient a compound of the formula (I), or a salt thereof, in admixture with a solid or liquefied gaseous diluent or carrier or in admixture with a liquid diluent or carrier containing a surface-active agent.

The invention also provides a method of combating arthropods, especially insects or acarids, which comprises applying to the arthropods, or to a habitat thereof, a compound of the formula (I), or a salt thereof, alone or in the form of a composition containing as active ingredient a compound of the formula (I) or a salt thereof, in admixture with a diluent or carrier.

Surprisingly, the chromane derivatives of the general formula (I) exhibit substantially better development-inhibiting properties than the compounds of similar structure and of analogous type of action known from the prior art. The active compounds according to the invention thus represent an enrichment of the art.

Some of the active compounds according to the invention are known (see German Offenlegungsschrift (German Published Specification) No. 2,639,671). An insecticidal action of these compounds has not been disclosed.

New compounds of the general formula (I), in which the radical X represents OH, are obtained by reducing the corresponding known chroman-4-ones of the general formula

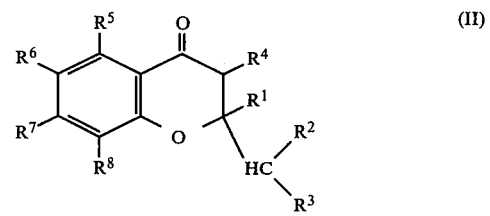

(II)

in which R¹ to R⁸ have the above-mentioned meanings.

The reduction of the chromanones of the general formula (II) to the chromanols of the general formula (I), in which X represents OH, can be carried out with metal hydrides or with complexes of metal hydrides, for example with boron hydride, sodium borohydride, lithium aluminum hydride or the borane/dimethylamine complex. This reaction is preferably carried out in a solvent which is inert towards the reducing agent in question, for example in a hydrocarbon (such as benzene or toluene), an ether (such as diethyl ether, tetrahydrofuran or dioxane), an alcohol (such as methanol, ethanol or glycol monomethyl ether) or a mixture of these solvents. The reaction is carried out at temperatures of from −20° C. to ±100° C., preferably from 0° C. to 40° C. (see Wagner-Zook, Synthetic Organic Chemistry, page 149, John Wiley & Sons Inc., New York 1953). The reduction can also be carried out with hydrogen in the presence of hydrogenation catalysts, especially with finely divided heavy metal catalysts, such as platinum, palladium, nickel or cobalt (see Wagner-Zook, Synthetic Organic Chemistry, page 149, John Wiley & Sons, Inc., New York 1953). The hydrogenation can optionally be carried out under elevated pressure and optionally in the presence of a solvent, for example in the presence of a hydrocarbon (such as benzene, toluene or cyclohexane), an ether (such as diethyl ether, dibutyl ether, tetrahydrofuran or dioxane), an alcohol (such as methanol, ethanol or glycol monomethyl ether) or a mixture of these.

New compounds of the general formula (I) in which the radical X represents —NR⁹R¹⁰ can be obtained if (a) chroman-4-ones of the general formula (II) are subjected to reducing conditions in the presence of amines of the general formula

HNR⁹R¹⁰ (III), in which R⁹ and R¹⁰ have the above-mentioned meanings, or (b) 4-halogenochromanes or 4-sulphonyloxychromanes of the general formula

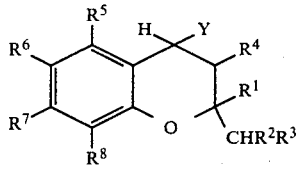

in which
R¹ to R⁸ have the above-mentioned meanings and
Y represent halogen or —O—SO₂R¹¹,
wherein
R¹¹ represents alkyl, cycloalkyl, aralkyl or aryl, are reacted with amines of the general formula (III), or (c) 4-aminochromanes of the general formula (I), in which
X represents —NR⁹R¹⁰,
wherein the radical R¹⁰ represents hydrogen, are reacted with compounds of the general formula

R¹⁰—Y (V), in which R¹⁰ and Y have the above-mentioned meanings, or (d) compounds of the general formula

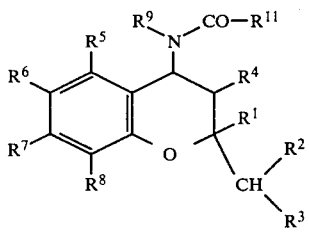

in which R¹ to R⁹ and R¹¹ have the above-mentioned meanings, are treated with reducing agents, especially mixed metal hydrides, such as lithium aluminum hydride or sodium borohydride, or (e) 4-aminochromanes of the general formula (I), in which X represents —NR⁹R¹⁰ and at least one of the radicals R⁹ or R¹⁰ represents hydrogen, are reacted with aldehydes of the general formula

R₁₂—CHO (VII), in which R₁₂ represents an optionally substituted alkyl, aryl or aralkyl radical, under reducing conditions.

4-Aminochromanes of the formula (I), in which X represents —NR⁹R¹⁰ and R⁹ and R¹⁰ represent hydrogen, can also be obtained if 4-oximinochromanes of the general formula

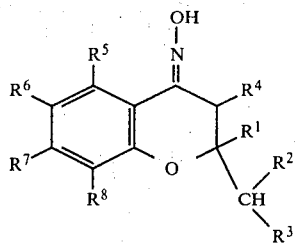

in which R¹ to R⁸ have the above-mentioned meanings, are reduced.

In the active compounds of the formula (I), preferred hydrocarbon radicals R¹ to R¹⁰ are straight-chain or branched alkyl radicals or alkenyl radicals with up to 18, preferably up to 12, especially up to 6, carbon atoms. As examples of alkyl or alkenyl radicals there may be mentioned methyl, ethyl, propyl, isopropyl, butyl, isobutyl, tert.-butyl, hexyl, nonyl, decyl, undecyl, octadecyl, but-3-enyl, 4-methylpent-3-enyl and 4,8-dimethylnona-3,7-dienyl. Preferred cycloalkyl radicals R¹ to R¹⁰ are those with 3 to 18, preferably with 4 to 12, especially with 5 or 6, carbon atoms, for example cyclopropyl, cyclobutyl, cycloheptyl, cyclooctyl, cyclododecyl, cycloheptadecyl, cyclooctadecyl and, preferably, cyclopentyl and cyclohexyl. Preferred aryl radicals R¹ to R¹⁰ are those with 6 to 14 carbon atoms, such as naphthyl, anthracencyl and, preferably, phenyl. Preferred aralkyl radicals are those with 7 to 18 carbon atoms of which the aliphatic part contains 1 to 8, preferably 1 to 4, carbon atoms and of which the aromatic part represents a carbocyclic radical with 6 to 10 carbon atoms, such as phenylethyl, phenylpropyl, phenylbutyl, naphthylmethyl, naphthylethyl and, preferably, benzyl.

Further preferred active compounds are those in which R¹ is bonded to R², to form an optionally substituted ring. This ring can be either carbocyclic or heterocyclic.

Examples of suitable carbocyclic rings are saturated or unsaturated rings containing hydrocarbon members, preferably 3-membered to 12-membered rings. It is also possible for the carbocyclic rings to be fused to one or more radicals from the benzene series.

As examples of carbocyclic rings there may be mentioned cyclopropane, cyclopentane, cyclohexane, cycloheptane, cyclooctane, cyclononane, cyclodecane, cycloundecane, cyclododecane, cyclohexene, cyclooctene, cyclododecene and tetralin.

Examples of suitable heterocyclic rings are 5-membered to 12-membered rings, preferably 5-membered and 6-membered rings, which in addition to hydrocarbon members also contain one or more hetero-atoms, for example nitrogen, oxygen or sulphur. The heterocyclic rings can contain 1 or 2 double bonds and can furthermore be fused to one or more radicals from the benzene series. As examples of heterocyclic rings there may be mentioned piperidine, pyrrolidine, tetrahydrofuran, tetrahydropyran and tetrahydrothiopyran.

The alkyl or aryl moieties of the preferred alkoxy, alkoxycarbonyl, alkylamino, dialkylamino, aryloxy and aralkoxy radicals correspond, in respect of their number of carbon atoms, to the ranges given above.

As preferred alkoxy groups there may be mentioned those with up to 4 carbon atoms, such as methoxy, ethoxy, propoxy, isopropoxy, butoxy, isobutoxy and tert.-butoxy.

As preferred aryloxy groups there may be mentioned those with 6 or 10 carbon atoms, such as phenoxy and naphthoxy.

As preferred aralkoxy groups there may be mentioned those with 7 to 10 carbon atoms, such as benzyloxy, phenylethoxy, phenylpropoxy, phenylisopropoxy, phenylbutoxy, phenylisobutoxy and phenyl-tert.-butoxy.

As preferred alkoxycarbonyl groups there may be mentioned those with up to 4 carbon atoms in the alkyl radical, such as methoxycarbonyl, ethoxycarbonyl, propoxycarbonyl and isopropoxycarbonyl.

As preferred alkylamino and dialkylamino groups there may be mentioned those with up to 3 carbon atoms in each alkyl radical, such as methylamino, ethylamino, isopropylamino, dimethylamino, diethylamino, dipropylamino and diisopropylamino. It is also possible for the two alkyl radicals of the dialkylamino group to be joined to form a ring, such as, for example, pyrrolidinyl or piperidinyl.

The acylamino group of the radicals $R^5$ to $R^8$ and $R^{11}$ can be substituted by an aliphatic or aromatic radical, in which case the aliphatic and the aromatic radical have the above-mentioned range of meanings. As examples of acylamino groups there may be mentioned formylamino, acetylamino, propionylamino, valeroylamino and benzoylamino.

Fluorine, chlorine, bromine and iodine, preferably chlorine, may be mentioned as halogens.

Suitable substituents of the alkyl, alkenyl, cycloalkyl, aryl, aryloxy, aralkyl, alkoxy, aralkoxy, alkoxycarbonyl, alkylamino and dialkylamino groups of the radicals $R^1$ to $R^{11}$ are substituents which do not undergo a change under the reaction conditions. Examples which may be mentioned are halogens, namely fluorine, chlorine, bromine and iodine, cyano, $C_1$-$C_6$-alkyl, $C_1$-$C_6$-alkoxy, ($C_1$-$C_6$-alkoxy)carbonyl, ($C_1$-$C_6$-alkoxy)carbonyl($C_1$-$C_6$-alkyl),amino, $C_1$-$C_6$-alkylamino, di-($C_1$-$C_6$-alkyl)amino, an aryl radical from the benzene series, or a carboxylic acid group.

Further preferred active compounds are those of the general formula (I), in which $R^9$ and $R^{10}$ form, with the adjoining N atom, a heterocyclic ring, for example pyrrolidine, piperidine, morpholine, N-methylpiperazine and N-phenylpiperazine.

The following active compounds of the general formula (I) should be mentioned particularly: 2,2-pentamethylenechroman-4-ol, 2,2-pentamethylene-7-hydroxychroman-4-ol, 2,2-pentamethylene-6-hydroxychroman-4-ol, 2,2-pentamethylene-6-methoxychroman-4-ol, 2,2-pentamethylene-7-methoxychroman-4-ol, 7-acetylamino-2,2-pentamethylenechroman-4-ol, 6-cyclohexyl-2,2-pentamethylenechroman-4-ol, 5-chloro-7-phenyl-2,2-pentamethylenechroman-4-ol, 7-alkoxy-2,2-pentamethylenechroman-4-ol, 6-ethoxycarbonylmethoxy-2,2-pentamethylenechroman-4-ol, 6-nitro-2,2-pentamethylenechroman-4-ol, 5-cyano-2,2-pentamethylenechroman-4-ol, 7-trifluoromethyl-2,2-pentamethylenechroman-4-ol, 6-carboxy-2,2-pentamethylenechroman-4-ol, 7-methoxycarbonyl-2,2-pentamethylenechroman-4-ol, 6-butyramido-2,2-pentamethylenechroman-4-ol, 7-amino-2,2-pentamethylenechroman-4-ol, 5-hydroxy-7-phenyl-2,2-pentamethylenechroman-4-ol, 2-methyl-2-($\gamma$-diethylaminopropyl)-chroman-4-ol, 2-methyl-2-($\beta$-carboxyethyl)-chroman-4-ol, 2-methyl-2-nonyl-7-hydroxy-chroman-4-ol, 2-methyl-2-($\beta$-N-pyrrolidinylethyl)-chroman-4-ol, 2-methyl-2-($\delta$-carboxybutyl)-chroman-4-ol, 2,2-tetramethylenechroman-4-ol, 7-hydroxy-2,2-tetramethylenechroman-4-ol, 6-hydroxy-2,2-tetramethylenechroman-4-ol, 8-methoxy-2,2-tetramethylenechroman-4-ol, 6-ethoxy-2,2-tetramethylenechroman-4-ol, 7-chloro-2,2-tetramethylenechroman-4-ol, 5-bromo-2,2-tetramethylenechroman-4-ol, 2-isopropyl-3-phenyl-6-methylchroman-4-ol, 2,3,6-trimethyl-chroman-4-ol, 5,7-dihydroxy-2,2-tetramethylenechroman-4-ol, 6,8-dihydroxy-2,2-tetramethylenechroman-4-ol, 5,8-dihydroxy-2,2-tetramethylenechroman-4-ol, 5,7,8-trihydroxy-2,2-tetramethylenechroman-4-ol, 7-benzyloxy-2,2-tetramethylenechroman-4-ol, 6-dimethylamino-2-isopropyl-chroman-4-ol, 7-acetamino-2-isopropyl-chroman-4-ol, 7-chloro-2-propyl-chroman-4-ol, 6-hexylamino-2-methyl-2-nonyl-chroman-4-ol, 5-hydroxy-7-pentyl-2,2-tetramethylenechroman-4-ol, 5-hydroxy-7-pentyl-2,2-undecamethylenechroman-4-ol, 5-hydroxy-7-heptyl-2-methyl-2-nonyl-chroman-4-ol, 5-methyl-7-hydroxy-2-methyl-2-$\delta$-carboxybutyl-chroman-4-ol, 6-hydroxy-2-methyl-2-$\delta$-carboxybutyl-chroman-4-ol, 7-hydroxy-2-$\delta$-carboxybutyl-chroman-4-ol, 5-hydroxy-7-pentyl-2-methyl-2-$\beta$-carboxyethyl-chroman-4-ol, 6-hydroxy-2-methyl-2-$\beta,\beta,\beta$-trifluoroethyl-chroman-4-ol, 2-methyl-2-N-pyrrolidinylpropyl-chroman-4-ol, 2-methyl-2-benzylchroman-4-ol, 2-hydroxy-butyl-chroman-4-ol, 6-chloro-8-methyl-2,2-tetramethylenechroman-4-ol, 6,8-dichloro-2,2-pentamethylene-chroman-4-ol, 4-methylamino-2,2-tetramethylenechromane, 4-dimethyl-amino-2,2-tetramethylenechromane, 4-ethyl-amino-2,2-tetramethylenechromane, 4-diethyl-amino-2,2-tetramethylenechromane, 4-dipropylamino-2,2-tetramethylenechromane, 4-isopropyl-amino-2,2-tetramethylenechromane, 4-diisopropyl-amino-2,2-tetramethylenechromane, 4-n-butyl-amino-2,2-tetramethylenechromane, 4-di-n-butyl-amino-2,2-tetramethylenechromane, 4-isobutyl-amino-2,2-tetramethylenechromane, 4-diisobutylamino-2,2-tetramethylenechromane, 4-tert.-butyl-amino-2,2-tetramethylenechromane, 4-(2'-ethylhexyl)-amino-2,2-tetramethylenechromane, 4-n-hexyl-amino-2,2-tetramethylenechromane, 4-octyl-amino-2,2-tetramethylenechromane, 4-dodecyl-amino-2,2-tetramethylenechromane, 4-hexadecylamino-2,2-tetramethylenechromane, 4-allyl-amino-2,2-tetramethylenechromane, 4-diallyl-amino-2,2-tetramethylenechromane, 4-(2-methoxyethyl)-amino-2,2-tetramethylenechromane, 4-(2-ethoxyethyl)-amino-2,2-tetramethylenechromane, 4-(3-methoxypropyl)-amino-2,2-tetramethylenechromane, 4-(2-cyanoethyl)-amino-2,2-tetramethylenechromane, 4-(3-cyanoethyl)-amino-2,2-tetramethylenechromane, 4-(2-phenoxyethyl)-amino-2,2-tetramethylenechromane, 4-(3-phenoxypropyl)-amino-2,2-tetramethylenechromane, 4-cyclopropyl-amino-2,2-tetramethylenechromane, 4-cyclobutyl-amino-2,2-tetramethylenechromane, 4-cyclopentyl-amino-2,2-tetramethylenechromane, 4-cyclohexylamino-2,2-tetramethylenechromane, 4-dicyclohexyl-amino-2,2-tetramethylenechromane, 4-cyclooctyl-amino-2,2-tetramethylenechromane, 4-cyclododecyl-amino-2,2-tetramethylenechromane, 4-phenyl-amino-2,2-tetramethylenechromane, 4-(2-chlorophenyl)-amino-2,2-tetramethylenechromane, 4-(3-chlorophenyl)-amino-2,2-tetramethylenechromane, 4-(4-chlorophenyl)-amino-2,2-tetramethylenechromane, 4-(2,4-dichlorophenyl)-amino-2,2-tetramethylenechromane, 4-(3,4-dichlorophenyl)-amino-2,2-tetramethylenechromane, 4-(2-methyl-phenyl)-amino-2,2-tetramethylenechromane, 4-(3-methyl-phenyl)-amino-2,2-tetramethylenechromane, 4-(4-methyl-phenyl)-amino-2,2-tetramethylenechromane, 4-(2,4-dimethylphenyl)-amino-2,2-tetramethylenechromane, 4-(3,4-dimethylphenyl)-amino-2,2-tetramethylenechromane, 4-(4-methoxyphenyl)-amino-2,2-tetramethylenechromane, 4-(3-ethoxyphenyl)-amino-2,2-tetramethylenechromane, 4-(2-isopropoxyphenyl)-amino-2,2-tetramethylenechromane, 4-(1-naphthyl)-amino-2,2-tetramethylene-chromane, 4-(2-naphthyl)-amino-2,2-tetramethylenechromane, 4-[1-(4-chloronaphthyl)]-amino-2,2-tetramethylenechromane, 4-[1-(4-bromonaphthyl)]-amino-2,2-tetramethylenechromane, 4-benzyl-amino-2,2 -tetramethylenechromane, 4-phenyl-ethylamino-2,2-tetramethylenechromane, 4-phenylpropyl-amino-2,2-tetramethylenechromane, 4-($\Delta^2$-cyclohexenyl)-amino-2,2-tetramethylenechromane, (4-$\Delta^3$-cyclohexenyl)-amino-2,2-tetramethylenechromane, 4-(4-chlorobenzyl)-amino-2,2-tetramethylenechromane, 4-(4-bromobenzyl)-amino-2,2-tetramethylenechromane, 4-(4-methoxybenzyl)-amino-2,2-tetramethylenechromane, 4-(4-methylbenzyl)-amino-2,2-tetramethylenechromane, 4-(naphthyl-1-methyl)-amino-2,2-tetramethylenechromane, 4-(naphthyl-2-methyl)-amino-2,2-tetramethylenechromane, 4-(4-bromophenylethyl)-amino-2,2-tetramethylenechromane, 4-(4-methoxyphenylethyl)-amino-2,2-tetramethylenechromane, 4-(4-chloro-phenylpropyl)-amino-2,2-tetramethylenechromane, 4-(4-methoxyphenylpropyl)-amino-2,2-tetramethylenechromane, 4-pyrrolidino-2,2-tetramethylenechromane, 4-piperidino-2,2-tetramethylenechromane, 4-(4-methyl-piperidino)-2,2-tetramethylenechromane, 4-(2,4,6-trimethyl-piperidino)-2,2-tetramethylenechromane, 4-morpholino-2,2-tetramethylenechromane, 4-(2,6-dimethylmorpholino)-2,2-tetramethylenechromane, 4-piperazino-2,2-tetramethylenechromane, 4-(4-methyl-piperazino)-2,2-tetramethylenechromane, 4-(4-phenyl-piperazino)-2,2-tetramethylenechromane, 4-(4-benzyl-piperazino)-2,2-tetramethylenechromane, 4-(2-diethylamino-ethyl)-amino-2,2-tetramethylenechromane, 4-(3-dimethylaminopropyl)-amino-2,2-tetramethylenechromane, 4-benzylamino-2,2-pentamethylenechromane, 4-benzylamino-2,2-pentamethylene-6-methoxychromane, 4-benzylamino-2,2-pentamethylene-7-methoxychromane, 4-benzylamino-2-methyl-2-nonyl-7-hydroxychromane, 4-benzylamino-2,2-tetramethylenechromane, 4-benzylamino-8-methoxy- 2,2-tetramethylenechromane, 4-benzylamino-7,8-dimethoxy-2,2-tetramethylenechromane, 4-benzylamino-6,7-dimethoxy-2,2-tetramethylenechromane, 4-benzylamino-2,3,6-trimethylchromane, 4-benzylamino-7-benzyloxy-2,2-tetramethylenechromane, 4-benzylamino-2,2-dimethyl-6,8-dichlorochromane, 4-benzylamino-2,2-tetramethylene-6-chloro-8-methylchromane, 4-benzylamino-2,2-pentamethylene-6-chloro-8-methylchromane, 4-benzylamino-2,2-tetramethylene-6-chlorochromane, 4-benzylamino-2,2-tetramethylene-7-methylchromane, 4-dimethylamino-2,3,6-trimethylchromane, 4-dimethylamino-2,2-tetramethylene-6-chloro-8-methylchromane, 4-dimethylamino-2,2-pentamethylene-6-chloro-8-methylchromane, 4-dimethylamino-2,2-tetramethylene-6-chlorochromane, 4-dimethylamino-2,2-tetramethylene-7-methylchromane, 4-dimethylamino-2,2-pentamethylenechromane, 4-dimethylamino-2,2-pentamethylene-6-methoxychromane, 4-dimethylamino-2,2-pentamethylene-7-methoxychromane, 4-dimethylamino-2,2-tetramethylenechromane, 4-dimethylamino-8-methoxy-2,2-tetramethylenechromane, 4-dimethylamino-7,8-dimethoxy-2,2-tetramethylenechromane, 4-dimethylamino-6,7-dimethoxy-2,2-tetramethylenechromane, 4-dimethylamino-5,6-benzo-2,2-tetramethylenechromane, 4-dimethylamino-7,8-benzo-2,2-tetramethylenechromane, 4-phenethylamino-2,2-pentamethylenechromane, 4-phenethylamino-2,2-pentamethylene-7-methoxychromane, 4-phenethylamino-2,2-tetramethylenechromane, 4-phenethylamino-7,8-dimethoxy-2,2-tetramethylenechromane, 4-phenethylamino-6,7-dimethoxy-2,2-tetramethylenechromane, 4-phenethylamino-2,2-dimethyl-6,8-dichlorochromane, 4-phenethylamino-2,2-tetramethylene-6-chloro-8-methylchromane, 4-phenethylamino-2,2-pentamethylene-6-chloro-8-methylchromane, 4-phenethylamino-2,2-tetramethylene-6-chlorochromane, 4-phenethylamino-2,2-tetramethylene-7-methylchromane, 4-α-naphthylmethylamino-2,2-tetramethylenechromane, 4-β-naphthylmethylamino-2,2-tetramethylenechromane, 4-α-naphthylethylamino-2,2-pentamethylenechromane, 4-α-naphthylethylamino-2,2-pentamethylene-6-methoxychromane, 4-α-naphthylethylamino-2,2-pentamethylene-7-methoxychromane, 4-α-naphthylethylamino-2,2-tetramethylenechromane, 4-α-naphthylethylamino-8-methoxy-2,2-tetramethylenechromane, 4-α-naphthylethylamino-7,8-dimethoxy-2,2-tetramethylenechromane, 4-α-naphthylethylamino-5,7-dimethoxy-2,2-tetramethylenechromane, 4-α-naphthylethylamino-2,2-tetramethylene-6-chloro-8-methylchromane, 4-α-naphthylethylamino-2,2-pentamethylene-6-chloro-8-methylchromane, 4-α-naphthylethylamino-2,2-tetramethylene-6-chlorochromane, 4-α-naphthylethylamino-2,2-tetramethylene-7-methylchromane, 4-β-naphthylethylamino-2,2-pentamethylenechromane, 4-β-naphthylethylamino-2,2-pentamethylene-6-methoxychromane, 4-β-naphthylethylamino-2,2-pentamethylene-7-methoxychromane, 4-β-naphthylethylamino-2,2-tetramethylenechromane, 4-β-naphthylethylamino-8-methoxy-2,2-tetramethylenechromane, 4-β-naphthylethylamino-7,8-dimethoxy-2,2-tetramethylenechromane, 4-β-naphthylethylamino-6,7-dimethoxy-2,2-tetramethylenechromane, 4-β-naphthylethylamino-2,2-tetramethylene-6-chloro-8-methylchromane, 4-β-naphthylethylamino-2,2-pentamethylene-6-chloro-8-methylchromane, 4-β-naphthylethylamino-2,2-tetramethylene-6-chlorochromane, 4-β-naphthylethylamino-2,2-tetramethylene-7-methylchromane, 4-α-naphthylmethylamino-2,2-pentamethylenechromane, 4-α-naphthylmethylamino-2,2-pentamethylene-6-methoxychromane, 4-α-naphthylmethylamino-2,2-pentamethylene-7-methoxychromane, 4-α-naphthylmethylamino-2,2-tetramethylenechromane, 4-α-naphthylmethylamino-8-methoxy-2,2-tetramethylenechromane, 4-α-naphthylmethylamino-7,8-dimethoxy-2,2-tetramethylenechromane, 4-α-naphthylmethylamino-6,7-dimethoxy-2,2-tetramethylenechromane, 4-α-naphthylmethylamino-2,2-tetramethylene-6-chloro-8-methylchromane, 4-α-naphthylmethylamino-2,2-pentamethylene-6-chloro-8-methylchromane, 4-α-naphthylmethylamino-2,2-tetramethylene-6-chlorochromane, 4-α-naphthylmethylamino-2,2-tetramethylene-7-methylchromane, 4-β-naphthylmethylamino-2,2-pentamethylenechromane, 4-β-naphthylmethylamino-2,2-pentamethylene-6-methoxychromane, 4-β-naphthylmethylamino-2,2-pentamethylene-7-methoxychromane, 4-β-naphthylmethylamino-2,2-tetramethylenechromane, 4-β-naphthylmethylamino-8-methoxy-2,2-tetramethylenechromane, 4-β-naphthylmethylamino-7,8-dimethoxy-2,2-tetramethylenechromane, 4-β-naphthylmethylamino-6,7-dimethoxy-2,2-tetramethylenechromane, 4-β-naphthylmethylamino-2,2-tetramethylene-6-chloro-8-methylchromane, 4-β-naphthylmethylamino-2,2-pentamethylene-6-chloro-8-methylchromane, 4-β-naphthylmethylamino-2,2-tetramethylene-6-chlorochromane and 4-β-naphthylmethylamino-2,2-tetramethylene-7-methylchromane.

Active compounds of the general formula (I), in which the radicals $R^1$ and $R^2$ together with the adjoining carbon atoms form a carbocyclic or heterocyclic ring, are new.

These new active compounds can be obtained in accordance with the above-mentioned methods of preparation.

The active compounds according to the invention, of the general formula (I), some of which are known, possess, as already mentioned, development-inhibiting properties in insects and arachnids. They can therefore be employed as insecticides and acaricides. They may also be employed in the veterinary medicine field.

The active compounds are well tolerated by plants, have a favorable level of toxicity to warm-blooded animls, and can be used for combating arthropod pests, especially insects or acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blatella germanica, Acheta domesticus,* Oryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp., and Linognathus spp.;

from the order of the Mallophaga, for example Trichodectes spp. and Damalinea spp.;

from the order of the Thysanoptera, for example *Mercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Fomoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilialis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna, varivestis,* Atomaria spp., *Oryzaephilus surinamensis,* Anthonomus spp., Sitophilus spp., *Otiorrhynchus sulcatus, Cosmopolites sordidus, Ceutherrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Castrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyoma spp., Hyalomma spp., Ixodes spp., Psoroptes spp., Chorioptes spp., Sarcoptes spp., Tarsonemus spp., *Bryobia praetiosa,* Panonychus spp. and Tetranycus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents, diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied aqueous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The invention also provides crops protected from damage by arthropods by being grown in areas in which immediately prior to and/or during the time of the growing a compound of the formula (I), or a salt thereof, was applied, alone or in admixture with a diluent or carrier.

It will be seen that the usual methods of providing a harvested crop may be improved by the present invention.

The compounds of the formula (I) can also be applied, in admixture with a diluent or carrier, to domesticated animals in order to free or protect them from ectoparasitical insects or acarids.

The preparation of some active compounds to be used according to the invention is described below:

1. Compounds of the general formula (I), in which X represents OH:

EXAMPLE 1

300 g of 2,2-tetramethylenechroman-4-one were dissolved in 1.5 liters of methanol and 50 g of sodium boranate were added in the course of two hours. The temperature was kept below 35° C. by cooling. The solution was additionally kept for 20 hours at 25° C. and was then concentrated; 2 liters of water were added, the product was extracted twice with toluene, the organic phase was washed with water, dried over sodium sulphate and filtered, and the filtrate was concentrated. The residue was distilled. Yield: 275 g (92% of theory) of 2,2-tetramethylenechroman-4-ol; boiling point 165° C./0.2 mm Hg, melting point 56°–58° C.

EXAMPLE 2

20 g of lithium aluminum hydride were stirred with 1 liter of ether, a solution of 200 g of 2,2-tetramethylenechroman-4-one in 500 ml of ether was added dropwise in the course of 1 hour at below 20° C., and the mixture was stirred for a further 24 hours at 25° C. 20 ml of water and 60 ml of 15% strength potassium hydroxide solution were then added dropwise, the mixture was stirred for a further 2 hours and was filtered, the filtrate was concentrated and the residue was distilled. 183 g (91% of theory) of the same product as in Example 1 were obtained.

EXAMPLE 3

230 g of 2,2-tetramethylenechroman-4-one were dissolved in 1 liter of methanol and hydrogenated in the presence of 30 g of Raney nickel for 6 hours under a hydrogen pressure of 150 atmospheres gauge at 120°–140° C. The reaction mixture was filtered and the filtrate was concentrated and distilled, giving 217 g (93% of theory) of the same product as in Example 1.

EXAMPLE 4

The procedure described in Example 1 was followed, but with ethanol as the solvent; the same chromanol was obtained in 89% yield.

The chromanols summarized in Table 1 were prepared analogously to Example 1. The substituents other than hydrogen are listed under $R^1$ to $R^8$.

ture. The toluene phase was washed with water, dried over sodium sulphate, filtered and concentrated. The residue was dissolved in 15 ml of methanol and after one

TABLE 1

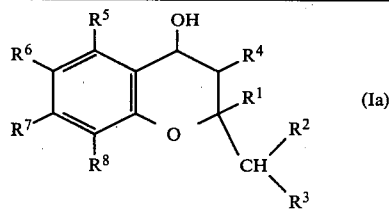

(Ia)

| Example | $R^1$ to $R^8$ | Yield | Boiling point (°C./ mm Hg) or melting point (°C.) |
|---|---|---|---|
| 5 | $R^1 + R^2 = -(CH_2)_3-$, $R^6 = Cl$ | 99% | 118°-120° C. |
| 6 | $R^1 + R^2 = -(CH_{23})-$, $R^7 = CH_3O$ | 98% | 160° C./0.1 |
| 7 | $R^2 = R^3 = CH_3$, $R^4 = C_6H_5$, $R^7 = CH_3O$ | 98% | ~40° C. |
| 8 | $R^1 + R^2 = -(CH_2)_4-$ | 99% | 150° C./0.2 |
| 9 | $R^1 + R^2 = -CH_2-CH_2-N(CH_3)-CH_2-$ | 77% | 123°-125° C. |
| 10 | $R^1 + R^2 = -(CH_2)_4-$, $R^7 = C_6H_5CH_2O-$ | 95% | 113°-115°C. |
| 11 | $R^2 = R^3 = CH_3$, $R^4 = C_6H_5$, $R^6 = CH_3$ | 98% | 132°-133° C. |
| 12 | $R^2 = n$-$C_5H_{11}-$ | 92% | 50-52° C. |
| 13 | $R^2 = C_6H_5-CH_2-$ | 99% | 44°-45° C. |
| 14 | $R^1 = -CH_2CH_2CH_2-N(C_2H_5)_2$ | 77% | 160°-5° C./0.1 |
| 15 | $R^1 = -CH_2-CH_2-N\underset{\diagup\diagdown}{\diagdown\diagup}$ | 51% | 100°-101° C. |
| 16 | $R^1 + R^2 = -(CH_2)_5-$, $R^6 = Cl$ | 79% | 82°-83° |
| 17 | $R^1 = (-CH_2)_3-N(C_2H_5)_2$, $R^7 = CH_3O$ | 88% | 185° C./0.1 |
| 18 | $R^1 = -CH_2-CH_2-CH=C(CH_3)_2$ | 76% | 160° C./0.1 |
| 19 | $R^2 = R^3 = CH_3$, $R^6 = R^8 = Cl$ | 98% | 75°-77° C. |
| 20 | $R^1 + R^2 = -(CH_2)_3-$ | 96% | 95°-97° C. |
| 21 | $R^2 = n$-$C_5H_{11}$, $R^7 = CH_3O$ | 65% | 170° C./0.2 |
| 22 | $R^2 = n$-$C_5H_{11}$, $R^7 = CH_3$ | 94% | 70°-72° C. |
| 23 | $R^2 = n$-$C_5H_{11}$, $R^6 = CH_3O$ | 98% | 66°-68° C. |
| 24 | $R^1 = C_6H_5-CH_2-CH_2-$ | 91% | 108° C./0.1 |
| 25 | $R^1 = -(CH_2)_3-CH(CH_3)-(CH_2)_2CH=C(CH_3)_2$ | 62% | 190° C./0.1 |
| 26 | $R^1 = -(CH_2)_3-N(C_2H_5)_2$, $R^6 = Cl$ | 88% | 180° C./0.2 |
| 27 | $R^2 = n$-$C_5H_{11}$, $R^6 = R^8 = Cl$ | 57% | 200° C./0.2 |
| 28 | $R^1 = n$-$C_9H_{19}$, $R^6 = R^8 = Cl$ | 51% | 190° C./0.1 |
| 29 | $R^1 = -(CH_2)_3-N(C_2H_5)_2$, $R^7 = C_6H_5-CH_2O-$ | 54% | 250° C./0.1 |
| 30 | $R^1 = R^7 = CH_3$ | 82% | 115° C./0.2 |
| 31 | $R^1 = CH_3$, $R^6 = Cl$ | 80% | 101°-103° C. |
| 32 | $R^1 + R^2 = -(CH_2)_3-$, $R^6 = C_6H_5-CH_2O$ | 75% | 74°-76° C. |
| 33 | $R^1 + R^2 = -(CH_2)_4-$, $R^6 = R^8 = Cl$ | 82% | 67°-69° C. |
| 34 | $R^1 = (CH_2)_2-CH=C(CH_3)_2$, $R^6 = R^8 = Cl$ | 69% | 165° C./0.1 |
| 35 | $R^1 = CH_3$, $R^6 = R^8 = Cl$ | 95% | 145° C./0.15 |
| 36 | $R^1 = -(CH_2)_3-N(C_2H_5)_2$, $R^6 = R^8 = Cl$ | 87% | 180° C./0.1 |
| 37 | $R^1 + R^2 = -(CH_2)_3-$, $R^5 = R^7 = R^8 = CH_3$ $R^6 = OH$ | 81% | >100° (decomposition) |
| 38 | $R^1 = COOH$ | 60% | oil |
| 39 | $R^1 + R^2 = -(CH_2)_3-$, $R^7 = C_6H_5$ | 81% | 91°-93° C. |
| 40 | $R^1 + R^2 = -(CH_2)_3-$, $R^6 = CH_3O$ | 93% | 155° C./0.1 |
| 41 | $R^1 + R^2 = -(CH_2)_3-$, $R^5/R^6 = $ benzo | 97% | 168°-170° C. |
| 42 | $R^1 + R^2 + R^2 = -(CH_2)_3-$, $R^7/R^8 = $ benzo | 93% | 145°-6° C. |
| 43 | $R^1 + R^2 = -(CH_2)_4-$, $R^6 = Cl$, $R^8 = CH_3$ | 92% | 170° C./0.25 |
| 44 | $R^1 + R^2 = -(CH_2)_3-$, $R^6 = Cl$, $R^8 = CH_3$ | 92% | 160° C./0.2 |
| 45 | $R^1 + R^2 = -(CH_2)_3-$, $R^6 = R^8 = NO_2$ | 72% | oil |
| 46 | $R^1 = (CH_2)_2 CH=C\begin{smallmatrix}CH_3\\ \\CH_3\end{smallmatrix}$, $R^5 = OH$ $R^7 = \underset{\diagdown\diagup}{\diagup N-\diagdown}$ | 42% | oil |

2. Compounds of the general formula (I) in which X represents $-NR^9R^{10}$:

EXAMPLE 47

15 g of 4-bromo-2,2-tetramethylenechromane were dissolved in 25 ml of toluene and 25 ml of morpholine were added, whereupon the internal temperature rose to 60° C. After one day, 100 ml of toluene and 50 ml of 2 N sodium hydroxide solution were added to the mixture.

day the product was filtered off. 11 g of 4-N-morpholino-2,2-tetramethylenechromane were obtained; melting point 88°-90° C.

(a) 4-Bromo-2,2-tetramethylenechromane used as a starting material was obtained as follows:

220 g of 2,2-tetramethylene-4-hydroxychromane were dissolved in 1 liter of ether, the solution was cooled to −20° C. and 220 g of phosphorus tribromide were added in the course of 60 minutes. The cooling was then stopped, the batch was additionally left for one day at room temperature, the ether phase was carefully poured onto sodium bicarbonate solution, the aqueous phase was separated off and the ether phase was washed twice with water. The ether solution was then dried over sodium sulphate, filtered and concentrated at below 30° C. 251 g of 4-bromo-2,2-tetramethylenechromane remained as an oil.

EXAMPLE 48

150 g of 2,2-tetramethylenechroman-4-one were dissolved in 500 ml of tetrahydrofuran and hydrogenated for 5 hours with hydrogen under a pressure of 125 atmospheres gauge at 150° C. in the presence of 30 g of Raney nickel and 300 ml of ammonia. After completion of the reaction, the catalyst was separated off, the solution was concentrated and the residue was distilled. Yield: 136 g of 4-amino-2,2-tetramethylenechromane; boiling point 130° C./0.2 mm Hg.

EXAMPLE 49

8 ml of acetic anhydride were added to a solution of the amine obtained in Example 48, in 50 ml of toluene. The mixture was left to stand for one day and the product was filtered off. 11.5 g of 4-acetylamino-2,2-tetramethylenechromane of melting point 187°–189° C. were obtained.

EXAMPLE 50

6 g of lithium aluminum hydride were stirred with 150 ml of glycol dimethyl ether, 18 g of the amide obtained according to Example 49 were added in portions and the mixture was then warmed to the reflux temperature for 9 hours. After it had cooled, 6 ml of water and 18 ml of 15% strength potassium hydroxide solution were added slowly at below 20° C., the product was filtered off, the filtrate was concentrated and the residue was distilled. 12 g of 4-ethylamino-2,2-tetramethylenechromane were obtained; boiling point 100° C./0.05 mm Hg.

EXAMPLE 51

A solution of 20 g of 2,2-tetramethylenechroman-4-one and 11 g of benzylamine in 100 ml of toluene was warmed under a water separator until no further water separated off (4 hours), and was then allowed to cool and was concentrated. The residue was dissolved in 100 ml of methanol and 4 g of sodium boranate were added. After one day, the batch was poured into water and the end product was extracted with toluene. After drying over sodium sulphate, the extract was concentrated, and distillation gave 17 g of 2,2-tetramethylene-4-benzylaminochromane; boiling point 180° C./0.1 mm Hg.

EXAMPLE 52

12 g of methanesulphonic acid chloride were added to a solution of 20 g of 4-hydroxy-2,2-tetramethylenechromane and 15 ml of triethylamine in 100 ml of toluene at 20° C. in the course of about 10 minutes. After one day, the mixture was poured into water, the toluene phase was separated off, dried over sodium sulphate and filtered, and the filtrate was concentrated at below 30° C. 30 ml of allylamine were added to the residue. After one day, the mixture was poured into 100 ml of 2 N NaOH, the toluene portion was separated off, dried over sodium sulpahte, filtered and concentrated, and the residue was distilled. 13 g of 4-allyl-amino-2,2-tetramethylenechromane were obtained; boiling point 135°/0.1 mm Hg.

EXAMPLE 53

8 g of lithium aluminum hydride were stirred with 300 ml of tetrahydrofuran, 40 g of 4-oximino-2,2-tetramethylenechromane were added in portions at below 30° C., and the mixture was heated for 3 hours to the reflux temperature and worked up analogously to Example 50. 29 g of 4-amino-2,2-tetramethylenechromane were obtained; boiling point 120°/0.2 mm Hg.

EXAMPLE 54

35 g of 2,2-pentamethylene-4-amino-6-methoxychromane were dissolved in 150 ml of methanol, 25 ml of a 70% strength solution of formaldehyde in methanol and 7 g of Raney nickel were added and hydrogenation was carried out for 4 hours at 110° C. under a hydrogen pressure of 150 atmospheres gauge. After the mixture had cooled, it was filtered, the filtrate was concentrated and distillation gave 27 g of 2,2-pentamethylene-4-dimethylamino-6-methoxychromane; boiling point 135°/0.1 mm Hg. On adding 150 ml of 2 N HCl, 38 g of the hydrochloride were obtained; melting point 243°–245° C.

In the table which follows, those of the radicals $R^1$ to $R^{10}$ which differ from hydrogen are listed.

TABLE 2

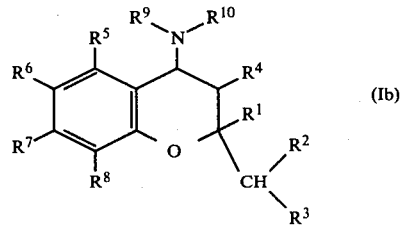

(Ib)

| Example | $R^1$ to $R^{10}$ | By Process of Example | Boiling point (°C./mm Hg) or melting point (°C.) |
|---|---|---|---|
| 55 | $R^1 + R^2 = -(CH_2)_3-$, $R^9 = R^{10} = CH_3$ | 54 | 220°–1° C. (as the hydrochloride) |
| 56 | $R^1 + R^2 = -(CH_2)_4-$, $R^7 = CH_3O$, $R^9 = R^{10} = CH_3$ | 54 | 192°–4° C. (as the hydrochloride) |
| 57 | $R^1 + R^2 = -(CH_2)_6-$, $R^9 = R^{10} = CH_3$ | 54 | 195°–7° C. (as the hydrochloride) |
| 58 | $R^2 = R^3 = R^9 = R^{10} = CH_3$ | 54 | 175–80/0.1 |
| 59 | $R^1 + R^2 = -(CH_2)_3-$, $R^9 = R^{10} = n\text{-}C_3H_7$ | 52 | 150/0.2 |
| 60 | $R^1 + R^2 = -(CH_2)_3-$, $R^9 = R^{10} = -(CH_2)_4-$ | 47 | 140/0.1 |
| 61 | $R^1 + R^2 = -(CH_2)_3-$, $R^9 = C_6H_5-CH_2-$ | 47 | 180/0.1 |
| 62 | $R^1 + R^2 = -(CH_2)_3-$, $R^9 = CH_2=CH-CH_2-$ | 47 | 130/0.05 |
| 63 | $R^1 + R^2 = -(CH_2)_3-$, $R^9 = $ -Pyridylmethyl | 47 | 150/0.2 |

TABLE 2-continued

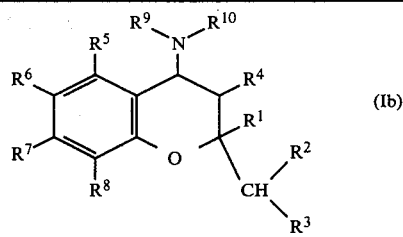

(Ib)

| Example | $R^1$ to $R^{10}$ | By Process of Example | Boiling point (°C./mm Hg) or melting point (°C.) |
|---|---|---|---|
| 64 | $R^1 + R^2 = -(CH_2)_3-$, $R^9 = C_6H_5-CH_2-CH_2$ | 47 | 210/0.3 |
| 65 | $R^1 + R^2 = -CH_2-CH_2-N(CH_3)-CH_2-$ | | 123 |
| 66 | $R^2 = R^3 = CH_3$ | | 115/0.2 |
| 67 | $R^1 + R^2 = -(CH_2)_3$, $R^9 = CH_3O-CH_2-CH_2-$ | 47 | 140/0.1 |
| 68 | $R^1 + R^2 = -(CH_2)_3$, $R^9 = n-C_6H_{13}$ | 52 | 150/0.1 |
| 69 | $R^1 + R^2 = -(CH_2)_3-$, $R^9 + R^{10} =$ Allyl | 47 | 130/0.1 |
| 70 | $R^1 + R^2 = -(CH_2)_3-$, $R^9 = (CH_3)_2N-(CH_2)_3-$ | 47 | 150/0.06 |
| 71 | $R^1 + R^2 = -(CH_2)_3-$, $R^9 = n-C_4H_9$ | 52 | 155/0.3 |
| 72 | $R^1 + R^2 = -(CH_2)_3-$, $R^9 = C_6H_5-$ | 47 | 85°-78° C. |
| 73 | $R^1 + R^2 = -(CH_2)_3-$, $R^9 = C_4H_9-CH(C_2H_5)-CH_2-$ | 47 | 170/0.1 |
| 74 | $R^1 + R^2 = -(CH_2)_3-$, $R^6 = R^8 = Cl$ $R^9 = C_4H_9-CH(C_2H_5)-CH_2-$ | 47 | 200/0.1 |
| 75 | $R^1 + R^2 = -(CH_2)_3-$, $R^6 = R^8 = Cl$, $R^9 =$ Allyl | 47 | 160/0.1 |
| 76 | $R^1 + R^2 = -(CH_2)_3-$, $R^6 = R^8 = Cl$, $R^9 = C_6H_5-CH_2-$ | 51 | 79-81 |
| 77 | $R^1 + R^2 = -(CH_2)_3$, $R^6 = R^8 = Cl$ $R^9 + R^{10} = -(CH_2)_4-$ | 47 | 80-82 |
| 78 | $R^1 + R^2 = -(CH_2)_3-$, $R^6 = R^8 = Cl$, $R^9 = CH_3O-CH_2-CH_2-$ | 47 | 165/0.1 |
| 79 | $R^1 + R^2 = -(CH_2)_3-$, $R^7 = Cl$, $R^9 = C_4H_9-CH(C_2H_5)-CH_2-$ | 47 | 190/0.05 |
| 80 | $R^1 + R^2 = -(CH_2)_3-$, $R^9 = (C_2H_5)_2N-CH_2-CH_2-$ | 47 | 150/0.1 |
| 81 | $R^1 + R^2 = -(CH_2)_3-$, $R^9 = R^{10} = (CH_3)_2N-(CH_2)_3-$ | 47 | 240/0.1 |
| 82 | $R^1 + R^2 = -(CH_2)_3-$, $R^9 + R^{10} = -CH_2-CH_2-N(CH_3)-(CH_2)_2-$ | 47 | 83-85 |
| 83 | $R^1 + R^2 = -(CH_2)_3-$, $R^{10} = \alpha$-naphthylmethyl | 47 | 220/0.1 |
| 84 | $R^1 + R^2 = -(CH_2)_3-$, $R^6 = Cl$, $R^9 = C_6H_5-CH_2-CH_2$ | 50 | 200/0.1 |
| 85 | $R^1 + R^2 = -(CH_2)_4-$, $R^6 = Cl$ $R^8 = CH_3$ $R^9 = C_6H_5-CH_2-CH_2-$ | 47 | 245/0.1 |
| 86 | $R^1 + R^2 = -(CH_2)_4-$, $R^6 = Cl$, $R^8 = CH_3 R^9 =$ benzyl | 47 | 210/0.1 |
| 87 | $R^1 + R^2 = (CH_2)_4-$, $R^6 = Cl$, $R^8 = CH_3$ $R^9 = \alpha$-naphthylmethyl | 47 | 112 |
| 88 | $R^1 + R^2 = -(CH_2)_3-$, $R^6 = Cl$, $R^8 = CH_3$ $R^9 =$ phenethyl | 50 | 210/0.1 |
| 89 | $R^1 + R^2 = -(CH_2)_3-$, $R^6 = Cl$, $R^8 = CH_3 R^9 =$ benzyl | 51 | 200/0.1 |
| 90 | $R^1 + R^2 = -(CH_2)_3-$, $R^6 = Cl$, $R^8 = CH_3$ $R^9 = \alpha$-naphthylmethyl | 47 | 98-100 |
| 91 | $R^1 + R^2 = -(CH_2)_3-$, $R^6 = CH_3O$, $R^9 = \alpha$-naphthylmethyl | 47 | 240/0.1 |
| 92 | $R^1 + R^2 = -(CH_2)_3-$, $R^6 = CH_3O$, $R^9 =$ phenethyl | 47 | 200/0.1 |
| 93 | $R^1 + R^2 = -(CH_2)_3-$, $R^6 = CH_3O$, $R^9 =$ benzyl | 47 | 190/0.1 |
| 94 | $R^1 + R^2 = -(CH_2)_3-$, $R^6 = CH_3$, $R^9 =$ benzyl | 47 | 230-1 (hydrochloride) |
| 95 | $R^1 + R^2 = -(CH_2)_3-$, $R^6 = CH_3$, $R^9 =$ phenylethyl | 47 | 201-2 (hydrochloride) |
| 96 | $R^1 + R^2 = -(CH_2)_3-$, $R^6 = CH_3$, $R^9 = \alpha$-naphthylmethyl | 47 | 216-8 (hydrochloride) |
| 97 | $R^1 + R^2 = -(CH_2)_3-$, $R^7 = CH_3$, $R^9 =$ benzyl | 47 | 204-6 (hydrochloride) |
| 98 | $R^1 + R^2 = -(CH_2)_3-$, $R^7 = CH_3$, $R^9 =$ phenylethyl | 47 | 201-3 (hydrochloride) |
| 99 | $R^1 + R^2 = -(CH_2)_3-$, $R^7 = CH_3$, $R^9 = \alpha$-naphthylmethyl | 47 | 208-10 (hydrochloride) |
| 100 | $R^1 + R^2 = -(CH_2)_3-$, $R^6 = Cl$, $R^9 =$ benzyl | 47 | 204-6 (hydrochloride) |
| 101 | $R^1 + R^2 = -(CH_2)_3-$, $R^6 = R^6 = Cl$, $R^9 = \alpha$-naphthylmethyl | 47 | 229-33 (hydrochloride) |
| 102 | $R^1 + R^2 = -(CH_2)_4-$, $R^9 =$ benzyl | 47 | 207-9 (hydrochloride) |
| 103 | $R^1 + R^2 = -(CH_2)_4-$, $R^9 =$ phenylethyl | 47 | 198-9 (hydrochloride) |
| 104 | $R^1 + R^2 = -(CH_2)_4-$, $R^9 = \alpha$-naphthylmethyl | 47 | 216-8 (hydrochloride) |

The arthropodicidal activity of the compounds of this invention is illustrated by the following examples wherein the compounds according to the present invention are each identified by the number (given in brackets) from the preparative examples hereinabove.

In the examples which follow, relating to the development-inhibiting action of the active compounds, the morphological changes, such as half-pupated animals, incompletely slipped larvae or caterpillars, defective wings, pupal cuticula in imagos and the like, over the course of the entire stated development of the test animals, were rated as malformations. The sum of the morphological malformations, together with the animals destroyed during shedding or metamorphosis, was determined as a percentage of the total number of test animals.

EXAMPLE 105

Development-inhibiting action/Laphygma egg test
 Test insect: *Laphygma frugiperda* (eggs)
 Solvent: 10 parts by weight of acetone
 Emulsifier: 1 part by weight of alkylaryl polyglycol ether To produce a suitable preparation of active compound, 2 parts by weight of active compound were mixed with the stated amounts of solvent and emulsifier and with sufficient water to produce a 1% strength mixture, which was diluted with water to the desired concentration.

Deposited eggs, at the rate of 30 eggs on a filter-paper, were moistened with 1 ml of active compound solution of the chosen concentration and were observed, in plastic boxes, until the young larvae slipped. The young larvae were fed with corn leaves which had been sprayed with the active compound solution of the chosen concentration on the same data as the eggs.

The development of the test insects was observed up to the larva of the 3rd stage.

As a control, deposited eggs were treated in the same manner with solvent and emulsifier-water mixture of the corresponding concentration, and feeding was carried out with correspondingly treated corn leaves.

In this text, the values shown in the table which follows were obtained:

TABLE 3

Development-inhibiting action/*Laphygma* egg test

Test insect: *Laphygma frugiperda* (eggs)

| Active compound | Development-inhibiting action (in %) at 0.01% concentration |
|---|---|
| Control: | 0 |
| Precocene I (known) | 0 |
| (18) | 100 |
| (55) | 100 |

EXAMPLE 106

Development-inhibiting action/ingestion test

Test insects: *Plutella maculipennis* (caterpillars in the 4th stage of development), 20 specimens *Phaedon cochleariae* (larvae in the 4th stage of development), 20 specimens Feed plants: Cabbage plants (*Brassica oleracea*)

Solvent: 10 parts by weight of acetone

Emulsifier: 1 part by weight of alkylaryl polyglycol ether

To produce a suitable preparation of active compound, 2 parts by weight of active compound were mixed with the stated amount of solvent and emulsifier and with sufficient water to give a 1% strength mixture, which was diluted with water to the desired concentration.

The test insects were fed with leaves of the feed plants, which were provided with a uniform spray covering of the active compound mixture, so that the chosen concentration of active compound (amount of compound per unit area) was obtained on the leaves, until the imago developed.

As a control, leaves coated only with solvent and emulsifier-water mixture of the chosen concentration were used as the feed.

In this test, the values shown in the table which follows are obtained:

TABLE 4

Development-inhibiting action/ingestion test

| Active compounds | Development-inhibiting action (%) at a concentration of 0.01% | |
|---|---|---|
| | *Plutella maculipennis* | *Phaedon cochleariae* |
| Control: Precocence I (known) | 60 | 0 |
| (55) | 100 | 100 |
| (72) | 100 | 60 |
| (75) | 100 | 100 |
| (66) | 100 | — |
| (12) | 100 | 100 |
| (19) | 100 | 80 |
| (20) | 100 | 100 |
| (21) | 100 | 80 |

TABLE 4-continued

Development-inhibiting action/ingestion test

| Active compounds | Development-inhibiting action (%) at a concentration of 0.01% | |
|---|---|---|
| | *Plutella maculipennis* | *Phaedon cochleariae* |
| (27) | 100 | 100 |
| (18) | 100 | — |
| (28) | — | 100 |

EXAMPLE 107

Test with parasitic scab mites (*Psoroptes cuniculi*)

Solvent: Alkylaryl polyglycol ether

To produce a suitable preparation of active compound, the active substance in question was mixed with the stated solvent in the ratio of 1:2 and the concentrate thus obtained was diluted with water to the desired concentration.

About 10–25 scab mites (*Psoroptes cuniculi*) were introduced into 1 ml portions of the active compound preparation to be tested, which had been pipetted into the tablet nests of a blister pack. After 24 hours, the degree of destruction in percent was determined. 100% meant that all of the mites had been killed and 0% meant that none of the mites had been killed.

Active compounds, active compound concentrations and results can be seen from the table which follows:

TABLE 5

Test with parasitic scab mites (*Psoroptes cuniculi*)

| Active compound | Active compound concentration ppm | Destructive action in % |
|---|---|---|
| (12) | 100 | 100 |
| (18) | 100 | 100 |
| (19) | 100 | 100 |
| (20) | 100 | 100 |
| (22) | 100 | 100 |
| (23) | 100 | 100 |
| (33) | 100 | 100 |
| (60) | 100 | 100 |
| (61) | 100 | 100 |
| (62) | 100 | 100 |
| (67) | 100 | 100 |
| (68) | 100 | 100 |
| (69) | 100 | 100 |
| (71) | 100 | 100 |
| (73) | 100 | 100 |

It will be appreciated that the instant specification and examples are set forth by way of illustration and not limitation, and that various modifications and changes may be made without departing from the spirit and scope of the present invention.

What we claim is

1. A chromane derivative of the formula

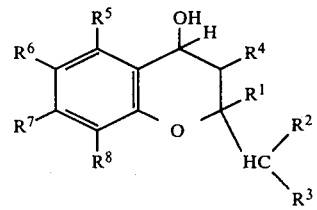

in which $R^1$ to $R^3$, which need not be identical, each represents hydrogen, or carboxyl, or an alkyl, alkenyl, cycloalkyl, phenyl, phenylalkyl or alkoxycarbonyl radical, any of these groups being optionally substituted by halogen, cyano, $C_1$-$C_6$-alkyl, $C_1$-$C_6$-alkoxy, ($C_1$-$C_6$-alkoxy)carbonyl, ($C_1$-$C_6$-alkoxy)carbonyl ($C_1$-$C_6$-alkyl), phenyl or a carboxylic acid group, $R^4$ represents phenyl, and $R^5$ to $R^8$, which need not be identical, each represents hydrogen, halogen, hydroxyl, nitro, cyano, carboxyl, an alkyl, alkenyl, cycloalkyl, phenyl, phenylalkyl, alkoxy, phenylalkoxy, phenoxy, alkoxycarbonyl, alkylamino or dialkylamino radical, amino or acylamino, and two of the radicals, which are in the o-position to one another, can represent tetramethylene or the radical —CH=CH—CH=CH—.

2. A compound according to claim 1, in which $R^1$ to $R^3$, which need not be identical, each represents $C_1$-$C_{18}$ alkyl, $C_2$-$C_{18}$ alkenyl, $C_3$-$C_{18}$ cycloalkyl, phenyl, phenylalkyl with 1 to 8 carbon atoms in the aliphatic part, or alkoxycarbonyl with 1 to 18 carbon atoms in the alkyl part, any of these groups being optionally substituted by halogen, cyano, $C_1$-$C_6$-alkyl, $C_1$-$C_6$-alkoxy, ($C_1$-$C_6$-alkoxy)-carbonyl, ($C_1$-$C_6$-alkoxy) carbonyl ($C_1$-$C_6$-alkyl) or a carboxylic acid group, or represents hydrogen or carboxyl, and $R^5$ to $R^8$, which need not be identical, each represents $C_1$-$C_{18}$ alkyl, $C_2$-$C_{18}$ alkenyl, $C_3$-$C_{18}$ cycloalkyl, phenyl, phenylalkyl or phenylalkoxy with 1 to 8 carbon atoms in the aliphatic part, $C_1$-$C_{18}$ alkoxy, phenoxy, alkoxycarbonyl with 1 to 18 carbon atoms in the alkyl part, $C_1$-$C_{18}$ alkylamino or di-($C_1$-$C_{18}$-alkyl) amino, or represents hydrogen, chlorine, hydroxyl, nitro, cyano, carboxyl, amino, aliphatic $C_1$-$C_{18}$ acylamino or benzoylamino, it being possible for two of the radicals $R^5$ to $R^8$ that are in the o-position to one another to represent tetramethylene or —CH=CH—CH=CH—.

3. A compound according to claim 1, in which said compound is 2-isopropyl-7-methoxy-3-phenyl-chroman-4-ol of the formula

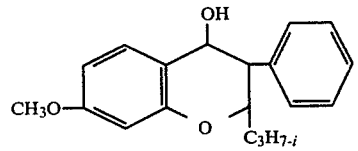

4. A compound according to claim 1, in which said compound is 2-isopropyl-6-methyl-3-phenyl-chroman-4-ol of the formula

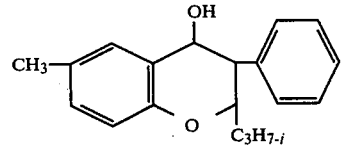

5. An arthropodicidal composition comprising an arthropodicidally effective amount of a compound according to claim 1 and a diluent.

6. A method of combating arthropods which comprises applying to the arthropods, or to a habitat thereof, an arthropodicidally effective amount of a compound according to claim 1.

* * * * *